US009090703B2

(12) United States Patent
Kobayashi et al.

(10) Patent No.: US 9,090,703 B2
(45) Date of Patent: Jul. 28, 2015

(54) SILK FIBROIN POROUS MATERIAL AND METHOD FOR PRODUCING SAME

(75) Inventors: Kazutoshi Kobayashi, Ibaraki (JP); Naosuke Sumi, Ibaraki (JP); Kazuo Kusaki, Ibaraki (JP); Tomoko Machida, Ibaraki (JP)

(73) Assignee: HITACHI CHEMICAL COMPANY, LTD., Tokyo (JP)

( * ) Notice: Subject to any disclaimer, the term of this patent is extended or adjusted under 35 U.S.C. 154(b) by 0 days.

(21) Appl. No.: 13/639,586

(22) PCT Filed: Apr. 5, 2011

(86) PCT No.: PCT/JP2011/058653
§ 371 (c)(1), (2), (4) Date: Oct. 5, 2012

(87) PCT Pub. No.: WO2011/126031
PCT Pub. Date: Oct. 13, 2011

(65) Prior Publication Data

US 2013/0109836 A1 May 2, 2013

(30) Foreign Application Priority Data

Apr. 6, 2010 (JP) ................................ 2010-088202
Apr. 6, 2010 (JP) ................................ 2010-088203
Oct. 6, 2010 (JP) ................................ 2010-227050
Oct. 6, 2010 (JP) ................................ 2010-227051

(51) Int. Cl.

| | |
|---|---|
| ***C07K 14/435*** | (2006.01) |
| ***A61K 8/64*** | (2006.01) |
| ***A61Q 19/00*** | (2006.01) |
| ***C08J 9/28*** | (2006.01) |

(52) U.S. Cl.
CPC ............ *C07K 14/43586* (2013.01); *A61K 8/64* (2013.01); *A61Q 19/00* (2013.01); *C08J 9/28* (2013.01); *C08J 2201/0544* (2013.01); *C08J 2207/10* (2013.01); *C08J 2389/00* (2013.01)

(58) Field of Classification Search
None
See application file for complete search history.

(56) References Cited

U.S. PATENT DOCUMENTS 7,727,575 B2 * 6/2010 Kaplan et al. .................. 427/2.1
2010/0055438 A1 3/2010 Kaplan et al.

FOREIGN PATENT DOCUMENTS

| | | |
|---|---|---|
| EP | 2 556 798 | 2/2013 |
| JP | 1-308431 | 12/1989 |
| JP | 2-109570 | 4/1990 |
| JP | 6-94518 | 4/1994 |
| JP | 8-41097 | 2/1996 |
| JP | 2000-045173 | 2/2000 |
| JP | 2001-259418 | 9/2001 |
| JP | 2002-186847 | 7/2002 |
| JP | 3412014 | 3/2003 |
| JP | 2003-175335 | 6/2003 |
| JP | 2003-192530 | 7/2003 |
| JP | 2006-249115 | 9/2006 |

OTHER PUBLICATIONS

Chen et al., “Synergic Combination of Collagen Matrix with Knitted Silk Scaffold Regenerated Ligament with More Native Microstructure in Rabbit Model”, 13th International Conference on Biomedical Engineering IFMBE Proceedings vol. 23, 2009, pp. 1195-1198.*
Ramshaw, J.A.M., “Gly-X-Y Tripeptide Frequencies in Collagen: A Context for Host-Guest Triple-Helical Peptides”, Journal of Structural Biology 122, 86-91 (1998).*
Yeo et al., “Collagen-Based Biomimetic Nanofibrous Scaffolds: Preparation and Characterization of Collagen/Silk Fibroin Bicomponent Nanofibrous Structures”, Biomacromolecules, 2008, 9, 1106-1116.*
Bolboaca et al., “Amino Acids Sequence Analysis on Collagen”, Bulletin USAMV-CN, 2007, 63-64, 311-316.*
Extended European Search Report, dated Nov. 25, 2014, including Supplementary European Search Report and European Search Opinion, for EP Application No. 11765931.8-1302/2557112 (PCT/JP2011/058653).

* cited by examiner

*Primary Examiner* — Suzanne M Noakes
(74) *Attorney, Agent, or Firm* — Fitch Even Tabin & Flannery

(57) ABSTRACT

By a silk fibroin porous material containing silk fibroin and an amino acid and a method for producing a silk fibroin porous material including freezing a fibroin solution having an amino acid added to a fibroin aqueous solution and subsequently thawing the solution to obtain a porous material, a porous material which does not contain a solvent and which is high in safety and a method for producing the same are provided.

25 Claims, 7 Drawing Sheets

SILK FIBROIN POROUS MATERIAL AND METHOD FOR PRODUCING SAME

TECHNICAL FIELD

The present invention relates to a silk fibroin porous material and a method for producing the same.

BACKGROUND ART

Porous materials capable of being prepared utilizing biological products such as proteins, sugars, etc. are utilized in a wide field in industry, inclusive of a medical field of wound covering material, hemostatic sponge, controlled drug release carrier, retractor, etc., a field of daily living necessaries such as paper diapers, sanitary napkins, etc., a field of water purification where such materials can be applied as a support serving as a den of microorganisms, bacteria, etc., a field of cosmetics or beauty treatment aiming at moisturizing or the like through the use by a beauty salon or an individual, a cell culture support or a tissue regeneration support in the tissue engineering or regenerative medical engineering, and the like.

As such a biological product constituting a porous material, there are known sugars such as cellulose, chitin, etc.; and a group of proteins such as collagen, keratin, fibroin, etc.

Among them, collagen has been most frequently utilized as the protein; however, it has become very difficult to utilize bovine-derived collagen since the BSE problem emerged. Furthermore, as for pig-derived collagen, there is involved a problem of new infectious diseases, and as for fish-derived collagen, there is involved a problem of strength of the porous material, so that it is difficult to put it into practical use. In addition, though keratin is obtainable from wool or feather, there is involved a problem of availability of raw materials, so that it is difficult to industrially utilize keratin. As for the wool, raw material prices are rising dramatically, and as for the feather, there is no marketplace, so that it is not easy to obtain raw materials. On the contrary, as for fibroin, it is possible to easily obtain fibroin from silk, and from the viewpoint of acquisition of raw materials, it can be expected that fibroin is stably supplied, and its price is stable, and hence, it is easy to industrially utilize fibroin.

Moreover, in addition to a clothing application, fibroin has a tract record that it has been long used as a surgical suture, and nowadays, fibroin is also utilized as additives for foods and cosmetics and is free from a problem regarding safety on the human body. Therefore, fibroin is sufficiently applicable to the utilization fields of porous materials as described above.

As for a technique for preparing a silk fibroin porous material, there are some reports. For example, there is proposed a method in which a fibroin aqueous solution is quickly frozen and then dipped in a crystallization solvent, and thawing and crystallization are allowed to simultaneously proceed, thereby producing a porous material of fibroin (Patent Document 1). However, according to this method, it is necessary to use a large amount of an organic solvent that is the crystallization solvent, and furthermore, a possibility of retention of the solvent may not be denied, so that there is involved a problem in the use of the method in the above-described application fields such as the medical field, etc.

In addition, there is proposed a method in which a fibroin aqueous solution is gelated while keeping it at a pH of not more than 6, or a poor solvent is added to that aqueous solution to achieve gelation, and the resulting gel is freeze-dried, thereby producing a porous material of fibroin (Patent Document 2). However, according to this method, it may be impossible to obtain a porous material with sufficient strength.

Furthermore, there is proposed a method in which after freezing a fibroin aqueous solution, its frozen state is kept for a long period of time, thereby producing a porous material (Patent Document 3). However, according to investigations made by the present inventors, this technique is poor in reproducibility, and in many cases, the porous material may not be prepared.

On the other hand, there is reported a method in which a porous material of fibroin with high strength is obtained surely and simply and easily as compared with the foregoing preparation techniques of a silk fibroin porous material (Patent Document 4 and Non-Patent Document 1). In Patent Document 4 and Non-Patent Document 1, it is disclosed that after adding a small amount of an organic solvent to a fibroin aqueous solution, the contents are frozen for a certain period of time and then thawed, whereby a hydrogel having a high water content and excellent mechanical strength may be produced.

PRIOR ART DOCUMENTS

Patent Documents

Patent Document 1: JP-A-8-41097
Patent Document 2: JP-B-6-94518
Patent Document 3: JP-A-2006-249115
Patent Document 4: Japanese Patent No. 3412014

Non-Patent Document

Non-Patent Document 1: *Biomacromolecules,* 6, 3100 to 3106 (2005)

SUMMARY OF THE INVENTION

Problems to be Solved by the Invention

As for the porous material prepared by the technique of Patent Document 4, a small amount of an organic solvent is also used in its production step. Therefore, according to investigations made by the present inventors, in order to remove the residual solvent, a washing step using dialysis with a large amount of ultra-pure water, or the like over a long period of time is essential. In addition, even if the solvent could be removed to a concentration of the detection limit or less by means of long-term washing, there is a concern that the residual solvent is contained in a trace amount of the detection limit or less, and there was involved such a problem that it may be impossible to use the porous material in the field where more safety is required.

Then, an object of the present invention is to provide a silk fibroin porous material which does not contain an organic solvent and which is excellent in safety and a method for producing a silk fibroin porous material not using an organic solvent.

Means for Solving the Problems

The present inventors made extensive and intensive investigations. As a result, it has been found that a porous material is obtained by freezing a solution having an amino acid added to a fibroin aqueous solution and then thawing the solution.

Specifically, the present invention is to provide a silk fibroin porous material containing silk fibroin and an amino acid as essential components and a method for producing a silk fibroin porous material comprising freezing a fibroin solution having an amino acid added to a fibroin aqueous solution and subsequently thawing the solution to obtain a silk fibroin porous material.

Effect of the Invention

According to the present invention, it is possible to simply and easily obtain a silk fibroin porous material with high safety.

MODES FOR CARRYING OUT THE INVENTION

Figure 1:
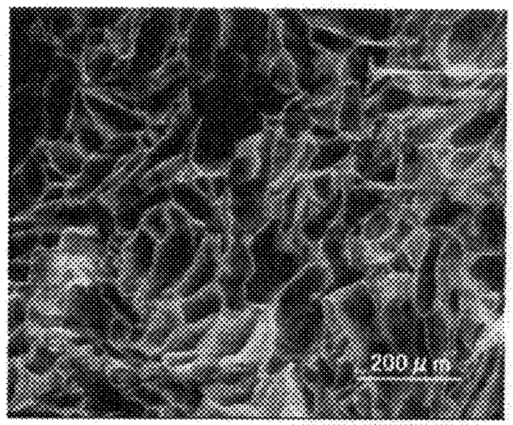
FIG. 1 is a scanning electron microscopic photograph of a cross section of a silk fibroin porous material prepared in Example 1.
Figure 2:
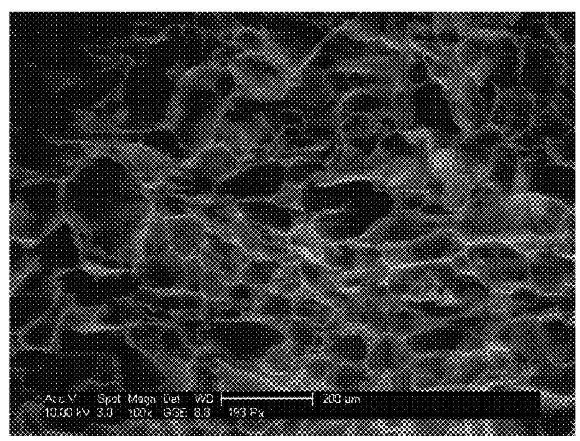
FIG. 2 is a scanning electron microscopic photograph of a cross section of a silk fibroin porous material prepared in Example 2.
Figure 3:
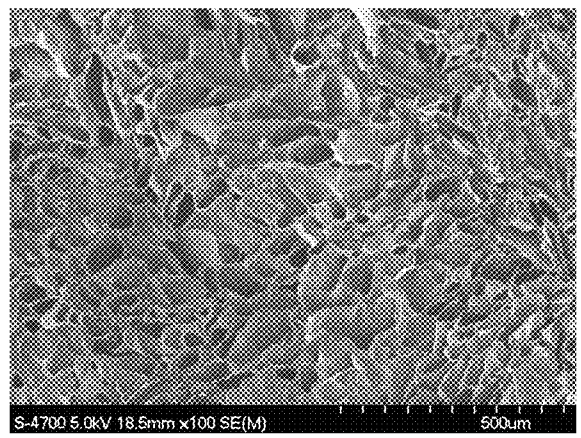
FIG. 3 is a scanning electron microscopic photograph of a cross section of a silk fibroin porous material prepared in Example 3.
Figure 4:
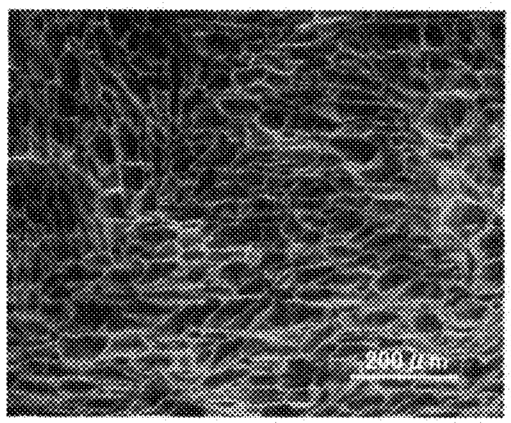
FIG. 4 is a scanning electron microscopic photograph of a cross section of a silk fibroin porous material prepared in Example 5.
Figure 5:
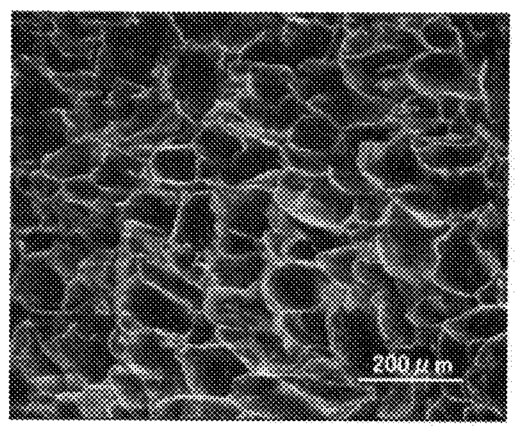
FIG. 5 is a scanning electron microscopic photograph of a cross section of a silk fibroin porous material prepared in Example 9.
Figure 6:
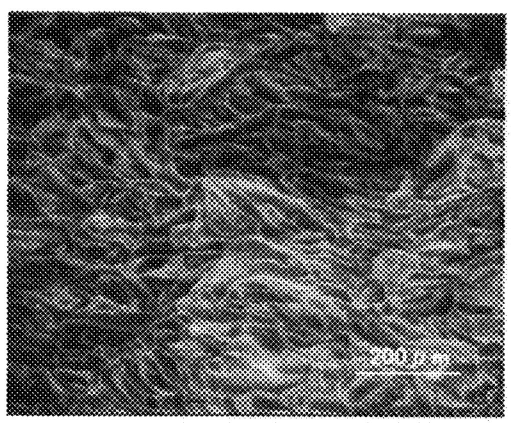
FIG. 6 is a scanning electron microscopic photograph of a cross section of a silk fibroin porous material prepared in Example 12.
Figure 7:
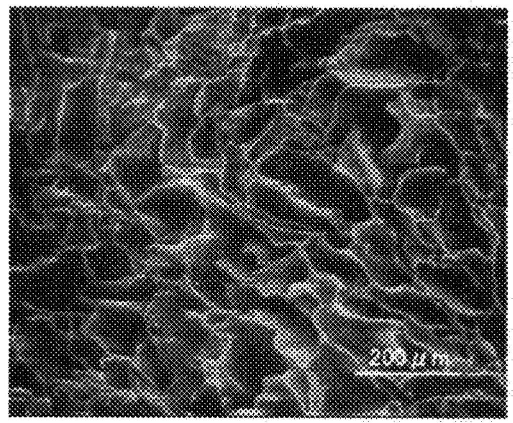
FIG. 7 is a scanning electron microscopic photograph of a cross section of a silk fibroin porous material prepared in Example 13.
Figure 8:
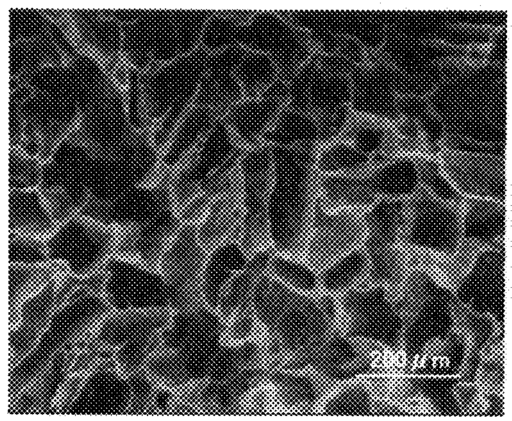
FIG. 8 is a scanning electron microscopic photograph of a cross section of a silk fibroin porous material prepared in Example 14.
Figure 9:
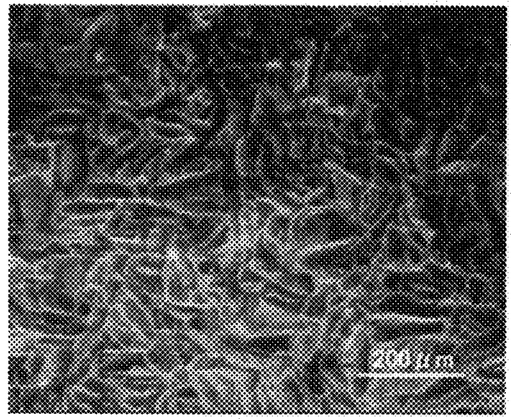
FIG. 9 is a scanning electron microscopic photograph of a cross section of a silk fibroin porous material prepared in Example 15.
Figure 10:
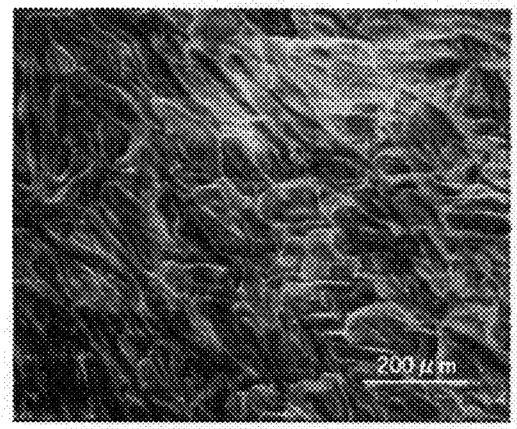
FIG. 10 is a scanning electron microscopic photograph of a cross section of a silk fibroin porous material prepared in Example 16.
Figure 11:
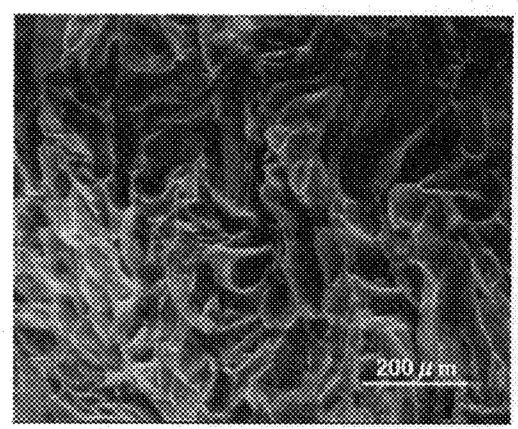
FIG. 11 is a scanning electron microscopic photograph of a cross section of a silk fibroin porous material prepared in Example 17.
Figure 12:
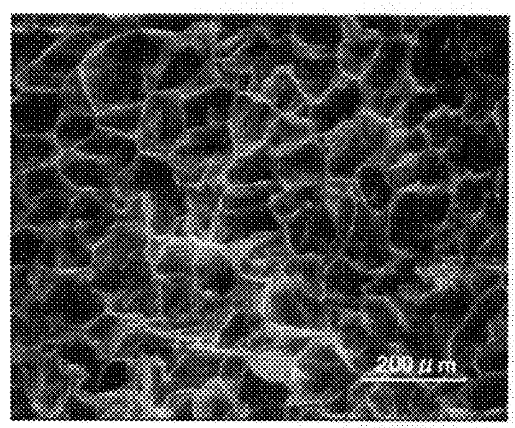
FIG. 12 is a scanning electron microscopic photograph of a cross section of a silk fibroin porous material prepared in Example 18.
Figure 13:
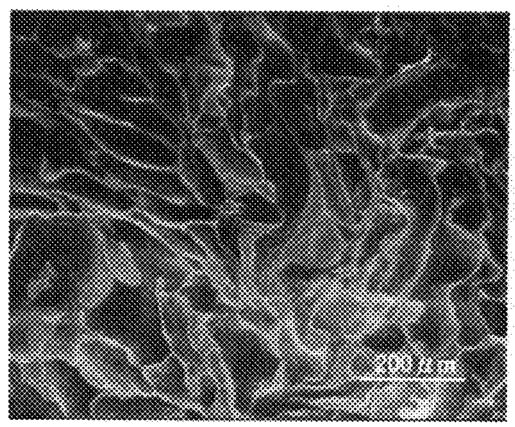
FIG. 13 is a scanning electron microscopic photograph of a cross section of a silk fibroin porous material prepared in Example 19.
Figure 14:
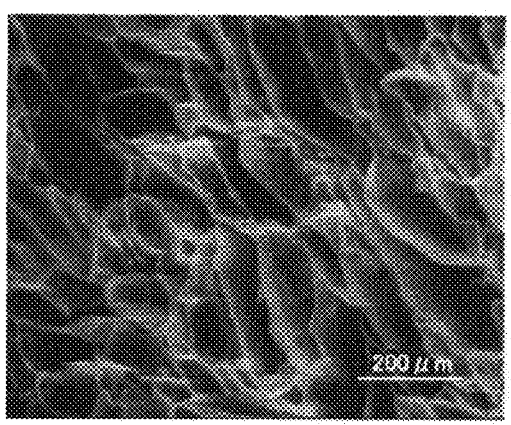
FIG. 14 is a scanning electron microscopic photograph of a cross section of a silk fibroin porous material prepared in Example 20.
Figure 15:
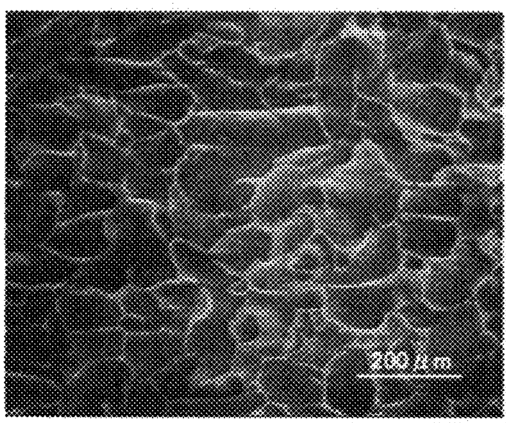
FIG. 15 is a scanning electron microscopic photograph of a cross section of a silk fibroin porous material prepared in Example 21.
Figure 16:
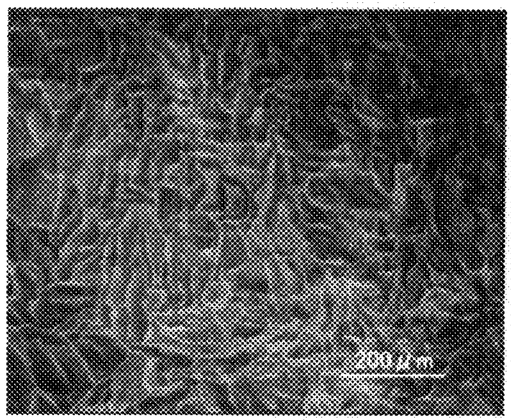
FIG. 16 is a scanning electron microscopic photograph of a cross section of a silk fibroin porous material prepared in Example 22.
Figure 17:
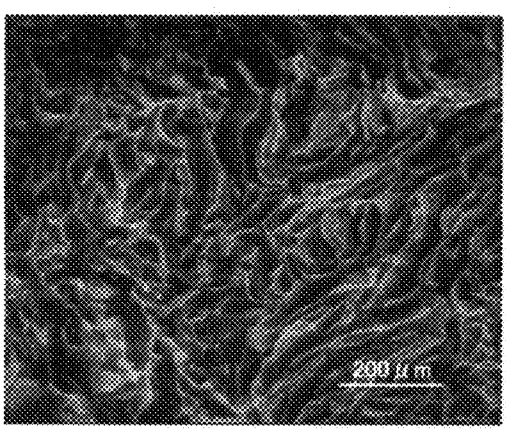
FIG. 17 is a scanning electron microscopic photograph of a cross section of a silk fibroin porous material prepared in Example 23.
Figure 18:
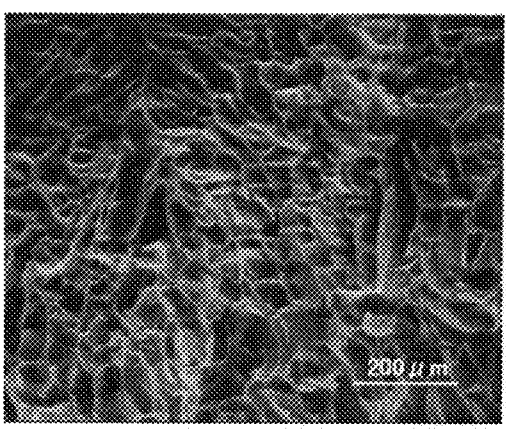
FIG. 18 is a scanning electron microscopic photograph of a cross section of a silk fibroin porous material prepared in Example 24.

The method for producing a silk fibroin porous material according to the present invention comprises freezing a fibroin solution having an amino acid added to a fibroin aqueous solution and then thawing the solution to obtain a porous material.

In addition, in the method for producing a silk fibroin porous material according to the present invention, it is possible to adjust a concentration of the amino acid by dipping and washing the porous material obtained after thawing in pure water. Here, as for the concentration of the amino acid remaining in the obtained silk fibroin porous material, the concentration of the amino acid which is added at the time of preparing a porous material is a maximum value and can be controlled from 0.01% by mass to the concentration of the added amino acid by a frequency or time of washing of the porous material, or the like. Alternatively, it is possible to obtain a porous material positively allowed to contain an amino acid by omitting the washing step.

The fibroin which is used in the present invention is preferably silk-derived fibroin which is produced from natural silkworms such as a domesticated silkworm, a wild silkworm, a Japanese oak silkworm, etc., or transgenic silkworms, and its production method does not matter. In the present invention, while fibroin is used as an aqueous solution thereof, the fibroin is poor in solubility in water, so that it is difficult to dissolve the fibroin directly in water. As a method for obtaining the fibroin aqueous solution, any known techniques may be adopted. However, a technique in which fibroin is dissolved in a high-concentration lithium bromide aqueous solution, and the solution is then subjected to desalting by means of dialysis and concentration by means of air-drying is simple and easy, and is preferable.

In the method for producing a silk fibroin porous material according to the present invention, a concentration of fibroin is preferably from 0.1 to 50% by mass, more preferably from 0.5 to 20% by mass, and still more preferably from 1 to 12 by mass in a fibroin solution to which an amino acid as described later has been added. By allowing the concentration of fibroin to fall within the foregoing range, it is possible to efficiently produce a porous material with sufficient strength. In addition, by adjusting a blending amount of silk fibroin, it is possible to obtain a silk fibroin porous material with strength according to the need. For example, when it is desired to obtain a silk fibroin porous material with higher strength, it may be possible to obtain it by increasing the blending amount of silk fibroin within a range of up to 50% by mass. However, the blending amount of silk fibroin is preferably from 30 to 50% by mass, and more preferably from 40 to 50% by mass.

Next, in the present invention, though the amino acid which is added to the fibroin aqueous solution is not particularly limited exclusive of noxious amino acids, amino acids which are soluble in water (water-soluble amino acids) are preferable, and amino acids with high solubility in water are more preferable.

Examples of the amino acid which is used in the present invention include aliphatic amino acids such as monoaminomonocarboxylic acids, for example, valine, leucine, isoleucine, glycine, alanine, serine, threonine, methionine, and the like, monoaminodicarboxylic acids (acidic amino acids), for example, aspartic acid, glutamic acid, and the like, diaminocarboxylic acids, for example, glutamine and the like, etc.; aromatic amino acids such as phenylalanine, tyrosine, etc.; amino acids having a heterocycle, such as proline, hydroxyproline, tryptophan, etc.; and the like. Of these, from the viewpoint of easiness of the adjustment of form or physical properties, acidic amino acids and oxyamino acids such as hydroxyproline, serine, threonine, etc. are preferable.

From the same viewpoint, among the acidic amino acids, monoaminodicarboxylic acids are more preferable, and aspartic acid and glutamic acid are especially preferable; and among the oxyamino acids, hydroxyproline is more preferable. Any one kind of these amino acids can be used solely, or a combination of two or more kinds thereof can be used.

In the production method according to the present invention, a blending amount of the amino acid is preferably from 0.01 to 18% by mass, more preferably from 0.1 to 5% by mass, and still more preferably from 0.5 to 2% by mass in the fibroin aqueous solution having the amino acid blended therewith.

From the viewpoint of preventing the precipitation of fibroin, the amino acid which is used in the present invention is preferably used as an aqueous solution. In the present invention, in the case of using an amino acid with low solubility in water, it is preferable to use an amino acid aqueous solution obtained by dissolving the amino acid in heated water and then cooling the solution to not higher than 30° C. (for example, room temperature). In the case where the amino acid precipitates in this cooling process, it is preferable to remove it by a method such as filtration, etc.

Incidentally, the amino acid includes L-type and D-type optical isomers. In the present invention, since when using the L-type and the D-type, there is not observed a difference between the resulting porous materials, any of these amino acids may be used.

In the production method according to the present invention, in particular, in the case of using an acidic amino acid, by allowing the silk fibroin aqueous solution having an acidic amino acid added to a silk fibroin aqueous solution to stand at a temperature at which the solution is not solidified prior to freezing, it is possible to obtain a silk fibroin porous material with higher strength. This standing of the silk fibroin aqueous solution having an acidic amino acid added thereto may be conducted under a prescribed temperature condition upon casting the subject aqueous solution into a mold or a container.

The temperature at the time of conducting the standing is not particularly limited so far as it is a temperature at which the subject aqueous solution is not solidified. However, taking into consideration the matter that solidification hardly occurs, gelation of the solution hardly occurs, or decomposition of the fibroin molecule hardly occurs, the temperature is preferably from −5 to 50° C., more preferably from −3 to 20° C., and still more preferably from 3 to 10° C. The temperature at which the standing is conducted can be adjusted by putting the silk fibroin aqueous solution into a thermostat, or other means. By adjusting the temperature at which the silk fibroin aqueous solution is allowed to stand, it is possible to adjust a pore diameter or strength of the obtained silk fibroin porous material. By adjusting the temperature to from 3 to 10° C., it is possible to obtain a porous material with small pore diameter and high strength.

Though a time for allowing the silk fibroin aqueous solution to stand is not particularly limited, by adjusting the time for conducting the standing, it is possible to obtain a silk fibroin porous material with strength according to the need. For example, if a porous material with higher strength is required, the time for conducting the standing is preferably 10 hours or longer, more preferably from 40 hours to 300 hours, and still more preferably from 50 hours to 300 hours.

In the method for producing a silk fibroin porous material according to the present invention, a fibroin solution having an amino acid added to a fibroin aqueous solution is cast into a mold or a container or the like and frozen upon being put into a low-temperature thermostat or the like, followed by thawing to produce a silk fibroin porous material.

As for a freezing method, the fibroin aqueous solution having an amino acid added thereto may be frozen by decreasing the temperature to a freezing temperature at once. However, from the standpoint of obtaining a silk fibroin porous material having a uniform structure, a method in which prior to the freezing, the fibroin aqueous solution having an amino acid added thereto is once held at from about 4 to −9° C., and preferably from about 0 to −5° C. for 30 minutes or longer to make the inside of the reactor uniform, and the temperature is then decreased to a freezing temperature is preferable. Furthermore, in the case where this holding temperature is adjusted to from about −1 to −9° C., and preferably from about −1° C. to −5° C., the fibroin aqueous solution reaches a temperature in a supercooled state (supercooling temperature) prior to the freezing, whereby a silk fibroin porous material having a more uniform structure can be obtained. In addition, by adjusting a time for holding at this supercooling temperature, adjusting a temperature gradient for decrease from the supercooling temperature to the freezing temperature, or other means, not only it is possible to obtain a silk fibroin porous material having a still more uniform structure, but it becomes possible to control the structure or strength of the porous material to some extent.

Subsequently, the frozen fibroin solution is thawed to obtain a porous material. A method for conducting the thawing is not particularly limited, and examples thereof include natural thawing, storage in a thermostat, and the like. Natural thawing is a simple and easy method.

Incidentally, by properly selecting the mold or container at the time of preparing a porous material, it is possible to fabricate the silk fibroin porous material obtained by the production method according to the present invention into a shape according to the object, such as a film form, a block form, a tubular form, etc. In addition, by adjusting the blending amount of the silk fibroin or amino acid to be used as the raw material, or selecting the kind of the amino acid, it is possible to adjust the internal structure and hardness of the silk fibroin porous material, and it is possible to obtain silk fibroin porous materials having different hardness levels in a gel form, a sheet form, or a block form.

While the obtained porous material contains an amino acid, in the case where it is necessary to remove the amino acid depending upon an application, the porous material can be used after removing the amino acid by a method such as standing in pure water, ultrasonic washing, etc. For example, a method for dipping the porous material in pure water to remove the amino acid is exemplified as the most simple and easy method.

In addition, as a method for adjusting a concentration of moisture after producing a silk fibroin porous material, for example, there is exemplified a method drying the silk fibroin porous material to evaporate the moisture. Examples of the drying method include natural drying, freeze-drying, heat-drying, and the like. From the viewpoint of suppressing shrinkage at the time of drying, freeze-drying is preferable.

The silk fibroin porous material obtained by the production method according to the invention has a spongiform porous structure, and in general, this porous material contains water and is in a hydrated state. The moisture contained in the porous material can be controlled by means of natural drying, freeze-drying, heat-drying, or the like. From the viewpoint of suppressing shrinkage at the time of drying, freeze-drying is preferable.

A size of pores (pore diameter) in the porous material obtained by the production method according to the present invention is from about 1 to 300 μm. The pore size can be controlled to some extent by adjusting a mixing ratio between fibroin and the amino acid, or a condition of a cooling process at the time of conducting the freezing as described above and is determined depending upon an application. In particular, by conducting the standing, it is possible to make the pore diameter extremely small as preferably from 1 to 50 μm.

Though a tensile elastic modulus of the silk fibroin porous material according to the present invention can be properly adjusted, it is usually from about 0.04 to 16 (MPa), and a porous material with appropriate hardness can be selected depending upon the application. For example, in an application in which a porous material with high strength is preferable, it is preferable to adjust a concentration of the silk fibroin aqueous solution at the time of preparing a silk fibroin porous material to 20% or more. In this way, a porous material with very high strength is obtained. Here, by adding an acidic amino acid to the silk fibroin aqueous solution and then allowing the solution to stand, it is also possible to more increase the strength. In an application where a soft porous material is preferable, it is preferable to adjust a concentration of the silk fibroin aqueous solution at the time of preparing a silk fibroin porous material to from 1 to 5%. In this way, a soft porous material is obtained. In addition, the tensile elastic modulus as referred to herein is one determined from a gradient of a graph between strength and strain at the time of cutting out a test piece of 40 mm×4 mm×4 mm from the silk fibroin porous material according to the present invention and drawing this test piece under a condition of 2 mm/min.

In addition, by adjusting the concentration of the silk fibroin aqueous solution which is used for the preparation of a silk fibroin porous material, it is possible to properly adjust a porosity of the silk fibroin porous material according to the present invention depending upon the application. For example, in an application where a high porosity is required, it is preferable to adjust the concentration of the fibroin aqueous solution to not more than 10% by mass. In this way, it is possible to obtain a porous material having a porosity of 90% or more. The porosity as referred to herein is a value obtained in the following manner. First of all, the obtained porous material is allowed to stand in pure water for one day to completely suck up water and then weighed (wet weight); and thereafter, the porous material is freeze-dried to completely remove the moisture in the porous material and then again weighed (dry weight). Subsequently, on the assumption that a density of water is 1 g/cm$^3$, a density of fibroin is 1.2 g/cm$^3$, and a density of the silk fibroin porous material in a hydrated state is 1 g/cm$^3$, a value obtained according to the following equation was defined as the porosity of the silk fibroin porous material.

$$\text{Porosity}=\{(\text{Wet weight})-(\text{Dry weight})/1.2\}/(\text{Wet weight})\times 100$$

In this way, the silk fibroin porous material obtained in the production method according to the present invention has an extremely large porosity and exhibits excellent performances in various applications.

Since the silk fibroin porous material according to the present invention does not contain a solvent, it is high in safety. In consequence, it is possible to apply the silk fibroin porous material according to the present invention to the medical field or the field where the material is applied to the human body. In particular, in view of the fact that the silk fibroin porous material according to the present invention is high in water absorption, has a nice texture, and is free from a problem regarding safety, it can be widely applied to a field of cosmetics or beauty treatment aiming at moisturizing or the like. Specifically, the silk fibroin porous material according to the present invention can be suitably used as a peeling pack or a cosmetic puff. Moreover, since the amino acid is contained in the porous material, the silk fibroin porous material according to the present invention can be expected to have a moisturizing effect of horn and is especially useful for a skin care application or the like. Specifically, the silk fibroin porous material according to the present invention can be suitably used as a peeling pack or a cosmetic puff. In addition, by varying the shape of the container which is used for freezing, it is possible to easily obtain a desired shape, and therefore, for example, the silk fibroin porous material according to the present invention can be suitably used as a face mask in conformity with a shape of face.

In addition, as for the silk fibroin porous material according to the present invention, its weight can be controlled by varying the amount of water absorption, and there is no problem regarding safety. Therefore, for example, the silk fibroin porous material according to the present invention may be suitably used as a weight for retracting a biological tissue cut off under endoscopic observation.

Besides, in view of the fact that the silk fibroin porous material according to the present invention is high in strength and water absorption and is free from a problem regarding safety, it can be suitably used in a medical field of wound covering material, controlled drug release carrier, hemostatic sponge, etc., or a field of daily living necessaries as paper diapers, sanitary napkins, etc., or as a cell culture support or a tissue regeneration support in the tissue engineering or regenerative medical engineering, a support serving as a den of microorganisms, bacteria, etc. in a field of water purification application or environment, or the like.

In addition, among the silk fibroin porous materials according to the present invention, one in a gel form can be suitably used as a wound covering material or a cosmetic aiming at moisturizing, improvement of chapped skin, skin whitening, or the like.

As for the amino acid, various physiological effects are reported, and therefore, various effects caused by the amino acid are expected in the amino acid-containing silk fibroin porous material according to the present invention. Specific expected effects are described below.

As for amino acids such as L-arginine, L-serine, L-proline, L-hydroxyproline, etc., a wound healing-promoting effect by coating is reported. Therefore, the wound healing-promoting effect can be expected in wound covering materials and external preparation gels using the silk fibroin porous material according to the present invention, and an effect for improving or preventing chapped skin can be expected in skin care members using the same, such as a face mask, etc.

As for a lot of amino acids such as L-glutamic acid, L-aspartic acid, glycine, L-serine, L-lysine, L-proline, L-hydroxyproline, etc., a moisturizing effect on a skin by coating is reported. Therefore, the moisturizing effect can be expected in skin care members using the silk fibroin porous material according to the present invention, such as a face mask, etc.

As for a part of amino acids such as L-ornithine or salts thereof, etc., a skin-whitening effect by coating on a skin is reported. Therefore, the skin-whitening effect can be expected in skin care members using the silk fibroin porous material according to the present invention, such as a face mask, etc.

As for aromatic amino acids such as L-tyrosine, L-tryptophan, L-phenylalanine, etc., an ultraviolet ray absorbing effect is reported. Therefore, a sunburn-protecting effect, a skin-whitening effect, and the like can be expected in skin care members using the silk fibroin porous material according to the present invention, such as a face mask, etc.

The silk fibroin porous material produced by the above-described production method according to the present invention contains an amino acid derived from the production step. In consequence, the present invention also provides a silk fibroin porous material containing silk fibroin and an amino acid as essential components.

As for quantitative analysis on how extent the amino acid contained in the obtained silk fibroin porous material remains, it is possible to adopt the Van Slyke method, the ninhydrin method, the fluorescent labeling analysis, the capillary electrophoresis analysis, or the like. While the amino acid is an organic material composed of a carboxyl group and an amino group, techniques for detecting chiefly the amino group are well known. Among them, by using an automatic amino acid analyzer (for example, Hitachi's L-8500), it is possible to simply and easily conduct qualitative or quantitative analysis of the amino acid. In the automatic amino acid analyzer, the amino acid is separated by an ion exchange resin and then detected by means of ninhydrin coloration. As for the concentration of the amino acid remaining in the obtained silk fibroin porous material, the concentration of the amino acid which is added at the time of preparing a porous material is a maximum value, and it is possible to control the concentration of the amino acid in the porous material from 0.01% by mass to the concentration of the added amino acid by a frequency or time of washing after the preparation of a porous material, or the like. However, since there is a possibility that the whole of the used fibroin does not become a porous material component, but a part thereof remains, it is necessary to remove the fibroin from a test solution prior to the measurement by utilizing a filter or the like.

EXAMPLES

The present invention is hereunder more specifically described by reference to the following Examples, but it should be construed that the present invention is not limited to these Examples at all.

Example 1

Preparation of Fibroin Aqueous Solution 20 g of a fibroin powder (trade name: Silkpowder IM, manufactured by KB Seiren, Ltd.) was added to 400 mL of a 9M lithium bromide aqueous solution and stirred for dissolution at room temperature for 4 hours. After centrifugation (at 12,000 rpm for 5 minutes), a precipitated insoluble matter was removed by means of decantation, the residue was poured into a dialysis tube (Spectra/Por®1 Dialysis Membrane, manufactured by Spectrum Laboratories, Inc., MWCO: 6,000 to 8,000), and dialysis of 12 hours relative to 5 L of ultra-pure water sampled from a pure water production system (Direct Q-W, manufactured by Millipore Corporation) was repeated 5 times. Subsequently, the resultant was concentrated in the dialysis tube by means of air-drying until the volume decreased to about ⅛, thereby obtaining a silk fibroin aqueous solution.

2 mL of the obtained silk fibroin aqueous solution was fractionated into a polystyrene-made container and weighed, followed by freezing over 12 hours in a freezing compartment of a CFC-free refrigerator-freezer (R-Y370, manufactured by Hitachi, Ltd.) in which the inside temperature had been adjusted to about −20° C. in advance. The resultant was freeze-dried for 7 hours in a freeze-dryer (FDU-1200, manufactured by EYELA). The obtained dried product was taken out from the freeze-dryer and weighed within 30 seconds, thereby quantitatively determining a silk fibroin concentration (% by mass) in the silk fibroin aqueous solution from a weight reduction.

(Preparation of Amino Acid Aqueous Solution)

L-Aspartic acid (amino acid) was weighed out such that at the time of mixing with the above-prepared silk fibroin aqueous solution, a final concentration was 1% by mass, which was then added to pure water heated at 80° C., and the mixture was then stirred for dissolution for 10 minutes while heating so as to keep the temperature at 80° C. Thereafter, the resultant was allowed to stand and cooled to room temperature, thereby obtaining an L-aspartic acid aqueous solution (amino acid aqueous solution).

(Production of Silk Fibroin Porous Material)

To the above-described silk fibroin aqueous solution, the L-aspartic acid aqueous solution was added, thereby finally obtaining a silk fibroin solution having a silk fibroin concentration of 5% by mass and an L-aspartic acid concentration of 1 by mass.

This silk fibroin solution was cast into a mold made of an aluminum plate (inner size: 80 mm×40 mm×4 mm), which was then put in a low-temperature thermostat (NCB-3300, manufactured by EYELA) and freeze-stored.

As for freezing, the low-temperature thermostat was cooled to −5° C. in advance; the mold having the silk fibroin solution charged therein was put in the low-temperature thermostat and held for 2 hours; and thereafter, the resultant was cooled at a cooling rate of 3° C./hr over 5 hours until the temperature within the thermostat reached −20° C. and then held at −20° C. for 5 hours. The frozen sample was returned to room temperature by means of natural thawing and then taken out from the mold, thereby obtaining a silk fibroin porous material. This silk fibroin porous material was a rigid porous material keeping a shape of the container which was used as the mold.

As for the silk fibroin porous material obtained by the production method according to the present invention, though the obtained silk fibroin porous material can be used as it is depending upon the object for the use, L-asparagine remaining in the moisture in the porous material can also be removed. In the present Example, the obtained porous material was dipped in ultra-pure water, and the used ultra-pure water was exchanged twice a day for 3 days, thereby removing the used L-aspartic acid.

(Observation by Scanning Electron Microscope)

The structure of the obtained silk fibroin porous material was observed using a scanning electron microscope. XL30-

FEG, manufactured by Philips was used as the scanning electron microscope, and the measurement was carried out in a low-vacuum non-vapor deposition mode at an accelerating voltage of 10 kV. Incidentally, as for the structure of the silk fibroin porous material, the interior of the porous material which had been exposed by cutting but not the surface of the porous material was observed. A scanning electron microscopic photograph of a cross section of the obtained silk fibroin porous material is shown in FIG. 1. Incidentally, whatever a step of removing the used amino acid is present or absent, the internal structure of the obtained porous material is basically identical. In the porous material, pores were observed, and a size of the pores (pore diameter) was from about 10 to 300 μm.

(Tensile Elastic Modulus)

Mechanical characteristics of the silk fibroin porous material were evaluated using a micro tester 5548 Model, manufactured by INSTRON. The tensile elastic modulus was determined from a gradient of a graph between strength and strain at the time of cutting out a test piece of 40 mm×4 mm×4 mm from the prepared silk fibroin porous material and drawing this test piece under a condition of 2 mm/min. The obtained results are shown in Table 2. Incidentally, as for the tensile elastic modulus, an average value obtained by preparing five test pieces from a prepared porous material, further cutting out five test pieces from a silk fibroin porous material prepared on a different day, and measuring the ten test pieces, is shown.

(Porosity)

The obtained silk fibroin porous material was allowed to stand in pure water for one day to completely suck up water and then weighed (wet weight); and thereafter, the silk fibrous porous material was freeze-dried to completely remove the moisture in the porous material and then again weighed (dry weight). Subsequently, on the assumption that a density of water is 1 g/cm$^3$, a density of silk fibroin is 1.2 g/cm$^3$, and a density of the silk fibroin porous material in a hydrated state is 1 g/cm$^3$, a porosity of the silk fibroin porous material was measured according to the following equation. The obtained results are shown in Table 2.

$$\text{Porosity}=\{(\text{Wet weight})-(\text{Dry weight})/1.2\}/(\text{Wet weight})\times 100$$

Examples 2 to 11

Silk fibroin porous materials were obtained in the same manner as that in Example 1, except that in Example 1, the amino acid to be added, the silk fibroin concentration, and the standing condition in the case of conducting the standing were changed to those shown in Table 2, respectively. Similar to Example 1, the silk fibroin porous materials obtained in these Examples were a rigid silk fibroin porous material keeping a shape of the container which was used as the mold. As for the silk fibroin porous materials obtained in Examples 1, 2, 3, 5 and 9, scanning electron microscopic photographs of the internal cross sections of the silk fibroin porous materials observed in the same manner as that in Example 1 are shown in FIGS. 2, 3, 4 and 5, respectively. In addition, various physical properties were measured in the same manners as those in Example 1. The obtained results are shown in Table 2.

Examples 12 to 24

Silk fibroin porous materials were obtained in the same manner as that in Example 1, except that in Example 1, an amino acid shown in Table 1 was used in place of the L-aspartic acid. The silk fibroin porous materials are a silk fibroin porous material keeping a shape of the container which was used as the mold. The silk fibroin porous materials obtained in Examples 12 to 21 included the case of a soft porous material and the case of a porous material in a gel form.

In addition, the silk fibroin porous materials obtained in Examples 22 to 24 were a porous material in a gel form keeping a shape of the container which was used as the mold. As for the silk fibroin porous materials obtained in Examples 12 to 24, scanning electron microscopic photographs of internal cross sections of the porous materials observed in the same manner as that in Example 1 are shown in FIGS. 6 to 18, respectively. In the porous materials, pores were observed, and a size of the pores (pore diameter) was from about 10 to 300 μm.

Examples 25 and 26

Silk fibroin porous materials were obtained in the same manner as that in Example 1, except that in Example 1, as shown in Table 1, L-tyrosine and L-tryptophan were used, respectively in place of the L-aspartic acid. However, in the cooling process after dissolving each of L-tyrosine and L-tryptophan in pure water, precipitation of each of L-tyrosine and L-tryptophan occurred, and therefore, the precipitate was removed by means of filtration. The obtained silk fibroin porous materials were a porous material in a gel form keeping a shape of the container which was used as the mold.

Figure 19:
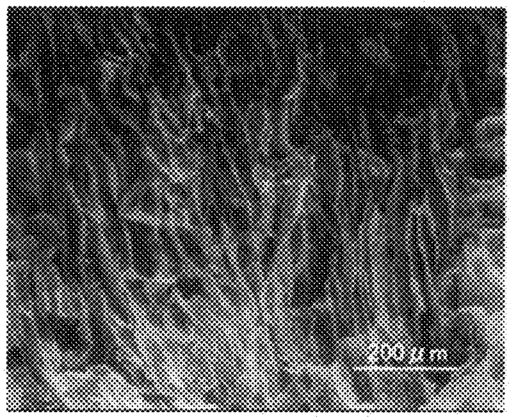
FIG. 19 is a scanning electron microscopic photograph of a cross section of a silk fibroin porous material prepared in Example 25.
Figure 20:
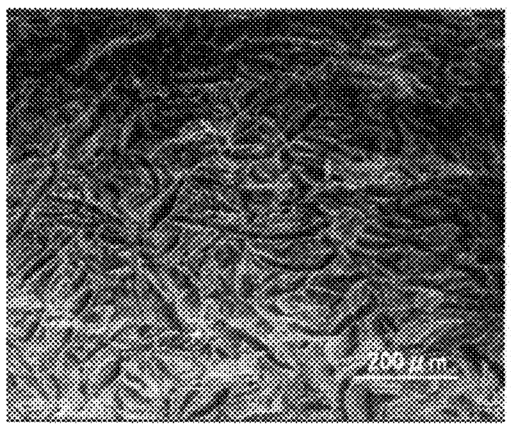
FIG. 20 is a scanning electron microscopic photograph of a cross section of a silk fibroin porous material prepared in Example 26.

Scanning electron microscopic photographs of internal cross sections of the porous materials observed in the same manner as that in Example 1 are shown in FIGS. 19 and 20, respectively. In all of these porous materials, pores were observed, and a size of the pores (pore diameter) was from about 10 to 300 μm.

Examples 27 to 29

Amino Acid Content

Qualitative or quantitative analysis of the amino acid contained in each of the obtained silk fibroin porous materials was conducted using an automatic amino acid analyzer (Hitachi's L-8500). In the automatic amino acid analyzer, the amino acid is separated by an ion exchange resin and then detected by means of ninhydrin coloration, and therefore, not only quantitative analysis but qualitative analysis may be conducted at the same time. However, since there is a possibility that the whole of the used silk fibroin does not become a porous material component, but a part thereof remains, the silk fibroin was removed from a test solution prior to the measurement.

In a final washing step with ultra-pure water of each of the silk fibroin porous materials prepared in Examples 1, 5 and 9, each sample was recovered before washing, after washing for 12 hours, after washing for 24 hours, after washing for 36 hours, after washing for 48 hours, after for 60 hours, and after for 72 hours, respectively, and the moisture contained in each of the silk fibroin porous materials was recovered. Subsequently, the silk fibroin was removed using an Amicon Ultra centrifugal filter kit, manufactured by Millipore Corporation (molecular weight cutoff: 5,000 and 10,000), and filtrates were recovered. These filtrates were measured by an automatic amino acid analyzer and subjected to qualitative or quantitative analysis of the amino acid contained therein. An amount of the sample was 10 μL; the ion exchange resin was #2622 that is a cation exchange resin; a column size at the time of separating the amino acid was 4.6 mm×60 mm; a column size at the time of trapping ammonia was 4.6 mm×40 mm; a flow rate was 0.30 mL/min; and visible lights of 570 nm and 440 nm were used for a detector. The obtained results are shown in Table 3. With respect to all of the Examples, it was noted that the amino acid in the silk fibroin porous material decreased with the washing time (frequency). In consequence, as for the concentration of the amino acid remaining in the obtained silk fibroin porous material, the concentration of the amino acid which is added at the time of preparing a porous material is a maximum value, and the concentration of the amino acid in the porous material can be controlled from zero to the concentration of the added amino acid by a frequency or time of washing after the preparation of a porous material, or the like. Incidentally, it may be considered that the reason why the concentration of the amino acid detected before washing was not more than the concentration of the amino acid added at the time of preparing a silk fibroin porous material resides in the matter that a part of the added amino acid was incorporated into the silk fibroin forming the porous material in some form (for example, adsorption, etc.).

TABLE 1

| | Added amino acid |
|---|---|
| Example 1 | L-Aspartic acid |
| Example 2 | L-Aspartic acid |
| Example 3 | L-Aspartic acid |
| Example 4 | L-Aspartic acid |
| Example 5 | L-Glutamic acid |
| Example 6 | L-Glutamic acid |
| Example 7 | L-Glutamic acid |
| Example 8 | L-Glutamic acid |
| Example 9 | L-Hydroxyproline |
| Example 10 | L-Hydroxyproline |
| Example 11 | L-Hydroxyproline |
| Example 12 | L-Serine |
| Example 13 | L-Threonine |
| Example 14 | L-Isoleucine |
| Example 15 | D-Phenylalanine |
| Example 16 | L-Phenylalanine |
| Example 17 | D-Methionine |
| Example 18 | L-Methionine |
| Example 19 | L-Proline |
| Example 20 | L-Leucine |
| Example 21 | L-Valine |
| Example 22 | Glycine |
| Example 23 | L-Alanine |
| Example 24 | L-Glutamine |
| Example 25 | L-Tyrosine |
| Example 26 | L-Tryptophan |
| Example 27 | L-Aspartic acid |
| Example 28 | L-Glutamic acid |
| Example 29 | L-Hydroxyproline |

TABLE 2

| | | Concentration of | Standing condition | | Tensile elastic | |
|---|---|---|---|---|---|---|
| | Added amino acid | silk fibroin (% by mass) | Temperature ° C. | Time (hr) | modulus (MPa) | Porosity (% by volume) |
| Example 1 | L-Aspartic acid | 5 | — | — | 0.252 | 96.0 |
| Example 2 | L-Aspartic acid | 2 | — | — | 0.045 | 98.4 |
| Example 3 | L-Aspartic acid | 20 | — | — | 5.80 | 83.2 |
| Example 4 | L-Aspartic acid | 20 | 3 | 50 | 14.6 | 83.2 |
| Example 5 | L-Glutamic acid | 5 | — | — | 0.289 | 96.0 |
| Example 6 | L-Glutamic acid | 2 | — | — | 0.053 | 98.3 |
| Example 7 | L-Glutamic acid | 20 | — | — | 5.91 | 83.1 |
| Example 8 | L-Glutamic acid | 20 | — | — | 16.0 | 83.0 |
| Example 9 | L-Hydroxyproline | 5 | — | — | 0.162 | 96.1 |
| Example 10 | L-Hydroxyproline | 2 | — | — | 0.031 | 98.5 |
| Example 11 | L-Hydroxyproline | 20 | — | — | 4.97 | 83.3 |

TABLE 3

| | | Addition | Concentration of amino acid (% by mass) | | | | | | |
|---|---|---|---|---|---|---|---|---|---|
| | Added amino acid | concentration of amino acid (% by mass) | Before washing | After washing for 12 hours | After washing for 24 hours | After washing for 36 hours | After washing for 48 hours | After washing for 60 hours | After washing for 72 hours |
| Example 27 | L-Aspartic acid | 1 | 0.68 | 0.39 | 0.28 | 0.23 | 0.20 | 0.18 | 0.17 |
| Example 28 | L-Glutamic acid | 1 | 0.80 | 0.43 | 0.28 | 0.22 | 0.18 | 0.15 | 0.13 |
| Example 29 | L-Hydroxyproline | 1 | 0.85 | 0.35 | 0.20 | 0.13 | 0.10 | 0.08 | 0.06 |

INDUSTRIAL APPLICABILITY

The silk fibroin porous material according to the present invention and the silk fibroin porous material obtained by the production method according to the present invention are excellent in safety, and therefore, they can be applied to the medical field or the field where the material is applied to the human body. Specifically, they can be widely applied to a field of cosmetics or beauty treatment or the like, and they are extremely useful as a face mask in conformity with a shape of face.

In addition, they can be applied to various industries inclusive of a medical field of wound covering material, controlled drug release carrier, hemostatic sponge, etc., or a field of daily living necessaries such as paper diapers, sanitary napkins, etc., or as a cell culture support or a tissue regeneration support in the tissue engineering or regenerative medical engineering, a support serving as a den of microorganisms, bacteria, etc. in a field of water purification application or environment, or the like.

The invention claimed is:

1. A silk fibroin porous material containing silk fibroin and a monomeric L-amino acid as components of the silk fibroin porous material.

2. The silk fibroin porous material according to claim 1, wherein the amino acid is an acidic amino acid.

3. The silk fibroin porous material according to claim 1, wherein the amino acid is an oxyamino acid.

4. The silk fibroin porous material according to claim 2, wherein the acidic amino acid is a monoaminodicarboxylic acid.

5. The silk fibroin porous material according to claim 4, wherein the monoaminodicarboxylic acid is aspartic acid or glutamic acid.

6. The silk fibroin porous material according to claim 3, wherein the oxyamino acid is hydroxyproline.

7. The silk fibroin porous material according to claim 1, the silk fibroin material itself having a spongiform porous structure, so as to provide the porous material.

8. The silk fibroin porous material according to claim 1, wherein the size of pores in the silk fibroin porous material is from about 1 to 300 μm.

9. The silk fibroin porous material according to claim 1, which does not contain an organic solvent.

10. The silk fibroin porous material according to claim 1, which includes at least 0.01% by mass amino acid, and up to a concentration of the amino acid added when preparing the porous material.

11. The silk fibroin porous material according to claim 1, wherein the amino acid is a water-soluble amino acid.

12. The silk fibroin porous material according to claim 1, wherein the material has been formed by casting in a mold or container.

13. The silk fibroin porous material according to claim 1, which has a tensile elastic modulus of from about 0.04 to 16 MPa.

14. The silk fibroin porous material according to claim 1, which consists essentially of said silk fibroin and said amino acid as components of the silk fibroin porous material.

15. The silk fibroin porous material according to claim 1, which consists of said silk fibroin and said amino acid as components of the silk fibroin porous material.

16. The silk fibroin porous material according to claim 1, prepared by providing a silk fibroin aqueous solution having amino acid as a component of the silk fibroin aqueous solution, freezing the silk fibroin aqueous solution having the amino acid as a component thereof, and thawing the silk fibroin aqueous solution having the amino acid as a component thereof, to obtain the silk fibroin porous material having the amino acid as a component of the silk fibroin porous material.

17. The silk fibroin porous material according to claim 16, wherein the amino acid has been added to the silk fibroin aqueous solution in an aqueous solution of the amino acid.

18. The silk fibroin porous material according to claim 16, wherein the silk fibroin aqueous solution having the amino acid as a component thereof, includes 0.01 to 18% by mass of the amino acid.

19. A method for producing a silk fibroin porous material comprising freezing a fibroin solution having a monomeric L-amino acid added to a fibroin aqueous solution and subsequently thawing the solution to obtain a porous material.

20. The method for producing a silk fibroin porous material according to claim 19, further including a step of dipping the porous material obtained after thawing in pure water to remove the amino acid.

21. The method for producing a silk fibroin porous material according to claim 19, not including a step of dipping the porous material obtained after thawing in pure water to remove the amino acid.

22. The method for producing a silk fibroin porous material according to claim 19, wherein the fibroin solution having an amino acid added thereto is held in a supercooled state for a certain period of time, prior to freezing.

23. The method for producing a silk fibroin porous material according to claim 19, wherein the fibroin solution having an amino acid added thereto is allowed to stand for 10 hours or longer at a temperature at which the solution is not solidified, prior to freezing.

24. The method for producing a silk fibroin porous material according to claim 19, wherein an addition amount of the amino acid is from 0.01 to 18% by mass in the fibroin solution.

25. The method for producing a silk fibroin porous material according to claim 19, wherein a concentration of fibroin is from 0.1 to 40% by mass in the fibroin solution having an amino acid added thereto.

* * * * *